Sept. 18, 1973 B. J. MACHIN Plant Pat. 3,401
CHRYSANTHEMUM PLANT
Filed Aug. 30, 1971
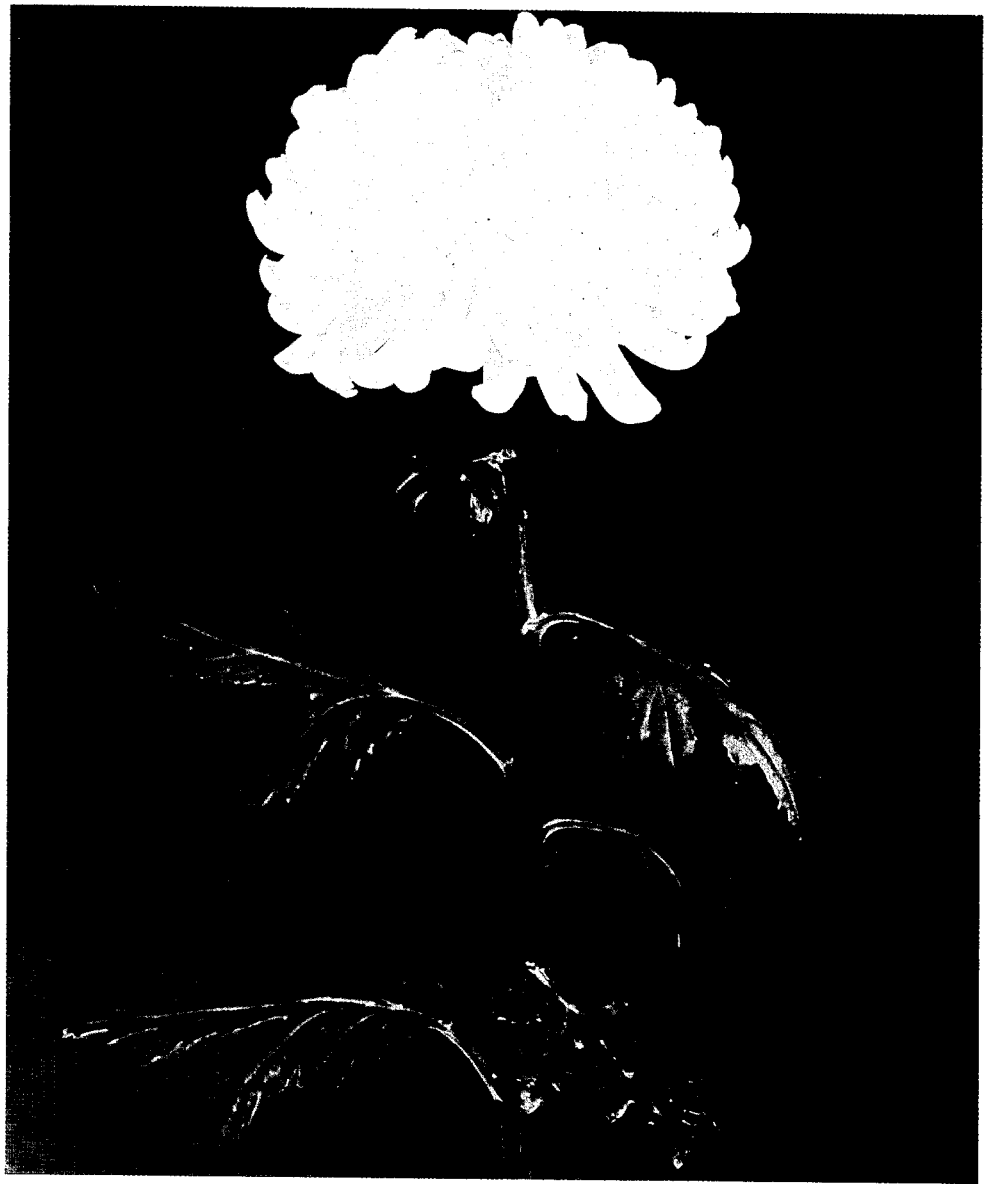

United States Patent Office

Plant Pat. 3,401
Patented Sept. 18, 1973

3,401
CHRYSANTHEMUM PLANT

Barrie John Machin, Chichester, England, assignor to Framptons Nurseries Limited, Sussex, England Filed Aug. 30, 1971, Ser. No. 176,340
Int. Cl. A01h 5/00
U.S. Cl. Plt.—77 1 Claim This invention relates to a new and distinct variety of *Chrysanthemum morifolium* Bailey (Standard type), hereinafter referred to as Snowdon.

Snowdon is a seedling originated by me from a cross made in 1964 between a seedling 33D4 (which originated from a cross between the varieties Explorer and Jonquil) and the variety Colombia, the former being the seed parent, the latter being the pollen parent.

The variety Snowdon resulted from an extensive breeding program with the object of producing improved year round standards for year round chrysanthemum production programs with improved uniformity and response as compared with existing varieties, with particular emphasis on winter production.

The following unique combination of characteristics distinguish Snowdon from the most similar white standard e.g. Mefo chrysanthemum varieties with which I am familiar:

(1) It is more responsive round the year, especially during poor light conditions and marginal temperature conditions. Flowering time in short days can be reduced by one week or ten days compared with Mefo according to season.

(2) Production is much more uniform and a higher grade of market flowers is obtained.

(3) There are fewer problems with damping off of flowers under humid conditions.

As compared with Mefo, the most similar year round standard chrysanthemum produced in Great Britain:

(1) Snowdon is more responsive the year round, especially under poor light and marginal temperature conditions, so that flowering time can be reduced by one week or ten days, according to season.

Although both Snowdon and Mefo are listed as varieties of 10 week response that is a convenient average measure to use. In fact, Snowdon tends to flower in 9 weeks in summer and 10 weeks in winter. Mefo takes 10 weeks in summer and up to 11½ weeks in winter in Europe.

This is why, although both are listed as 10 week varieties the response of Snowdon can be one week or 10 days in advance of Mefo in winter conditions.

(2) Production in Snowdon is more uniform and a higher grade of market flowers is produced.

(3) With Snowdon there are fewer problems with damping off of flowers under humid conditions.

(4) The flower size of Snowdon is slightly smaller, but the depth of flower is greater and therefore a more incurved shape of bloom is produced. Snowdon has more disc petals than Mefo, but even when the bloom is fully mature these are covered by the incurving inner ray petals.

As compared with its seed parent, Snowdon has smaller leaves and less vigorous vegetative characters which improve uniformity of production in poor light. Leaf color is darker. The petals are of firmer texture and broader.

As compared with its pollen parent, Snowdon has a flower nearer to pure white in color. The petals are of firmer texture. Foliage is much less likely to become chlorotic under different nutritional treatments. Snowdon can be grown round the year in European conditions whereas Columbia is a high light requiring variety.

Asexual reproduction of this new variety as performed in Sussex, England, by rooting vegetative shoots, shows that the above characteristics are fixed and come true to type and are transmitted through succeeding generations.

The accompanying drawing shows a typical flower of my new variety depicted in color as nearly true as it is reasonably possible to make the same in a color illustration of this character.

The following is a detailed description of the new variety Snowdon with color terminology in accordance with the Royal Horticultural Society Color Chart (R.H.S.).

Genus: Chrysanthemum
Species: *morifolium* Bailey
Type: Standard
Class: Incurving decorative
Breeding: Seedling. The cross between a year round seedling 33D4 and Columbia, the former being the seed parent and the latter being the pollen parent.
Locality where grown and observed: Forbridge Nursery, Chichester, Sussex, England
Propagation: Holds its distinguishing characteristics through succeeding propagations by rooting vegetative shoots.
Bloom size: Average diameter 13 cms. Average depth 11 cms. when fully open.
Petalage: 220 to 250 ray petals, 30 to 100 disc petals.
Form: Incurving decorative.
Petals: Broad overlapping, blunt boat-shaped with medium texture.
Color of open bloom: Inner face of fully expanded petal RHS 155B. Outer face of fully expanded petal RHS 155D. Inner face of young petal RHS 155B. Outer face of young petal RHS 155D.
Response group: 10 weeks.
Temperature tolerance: 55–60° F. at night.
Plant: Wiry upright habit of growth.
Foliage: Good quality. Average internode length 2½ to 3 cms. Small size color R.H.S. 137A; medium texture.
Stem: Medium thickness and wiry.
Color of stem at flowering: R.H.S. 146C.

I claim:

1. A new and distinct variety of *Chrysanthemum morifolium* Bailey, substantially as herein shown and described, characterized particularly as to novelty by the unique combination of a wiry, upright plant with incurving, decorative white flowers having from 220 to 250 ray petals and 30 to 100 disc petals, excellent resistance to damping off under humid conditions, and an improved response time of 1½ weeks during short day seasons in poor light conditions.

No references cited.

ROBERT E. BAGWILL, Primary Examiner